US012721834B2

(12) United States Patent
Myers et al.

(10) Patent No.: US 12,721,834 B2
(45) Date of Patent: Sep. 1, 2026

(54) COMBINATION TREATMENT FOR NETHERTON SYNDROME

(71) Applicant: Quoin Pharmaceuticals Inc., Ashburn, VA (US)

(72) Inventors: Michael Myers, Ashburn, VA (US); Denise Carter, Ashburn, VA (US)

(73) Assignee: Quoin Pharmaceuticals, Inc., Ashburn, VA (US)

( * ) Notice: Subject to any disclaimer, the term of this patent is extended or adjusted under 35 U.S.C. 154(b) by 343 days.

(21) Appl. No.: 18/428,570

(22) Filed: Jan. 31, 2024

(65) Prior Publication Data

US 2024/0252465 A1 Aug. 1, 2024

Related U.S. Application Data

(63) Continuation of application No. PCT/US2024/012940, filed on Jan. 25, 2024.

(60) Provisional application No. 63/481,535, filed on Jan. 25, 2023.

(51) Int. Cl.

| | |
|---|---|
| ***A61K 31/401*** | (2006.01) |
| ***A61K 9/00*** | (2006.01) |
| ***A61K 31/192*** | (2006.01) |
| ***A61K 31/196*** | (2006.01) |

(52) U.S. Cl.

CPC .......... *A61K 31/401* (2013.01); *A61K 9/0014* (2013.01); *A61K 31/192* (2013.01); *A61K 31/196* (2013.01)

(58) Field of Classification Search

CPC .. A61K 31/401; A61K 9/0014; A61K 31/192; A61K 31/196

USPC .......................................................... 514/423

See application file for complete search history.

(56) References Cited

U.S. PATENT DOCUMENTS

| | | | |
|---|---|---|---|
| 2013/0338198 | A1 | 12/2013 | Roszell |
| 2021/0162029 | A1 | 6/2021 | Sampson |

FOREIGN PATENT DOCUMENTS

| | | | |
|---|---|---|---|
| GB | 2450780 | A | 1/2009 |
| WO | 2005112989 | A1 | 12/2005 |
| WO | 2009093119 | A2 | 7/2009 |
| WO | 2015114144 | A1 | 8/2015 |

OTHER PUBLICATIONS

International Search Report and Written Opinion issued in PCT/US2024/012940 on Apr. 15, 2024.

Sonti, S , et al., "Efficacy of a Novel Treatment Serum in the Improvement of Photodamaged Skin", International Journal of Cosmetic Science, 2013, 35:156-162.

*Primary Examiner* — Kristin A Vajda

(74) *Attorney, Agent, or Firm* — Blank Rome LLP

(57) ABSTRACT

The present invention relates to methods of treating Netherton syndrome. In one embodiment, the method comprises administering to the patient (i) a serine protease inhibitor and (ii) an anti-inflammatory agent. In another embodiment, the method comprises (a) administering to the patient a serine protease inhibitor and an anti-inflammatory agent when the patient is having an outbreak of Netherton syndrome, and (b) administering a serine protease inhibitor when the patient is in remission. The present invention also relates to pharmaceutical compositions comprising (i) a serine protease inhibitor and (ii) an anti-inflammatory agent.

10 Claims, No Drawings

COMBINATION TREATMENT FOR NETHERTON SYNDROME

CROSS REFERENCE TO RELATED APPLICATIONS

The present application is a continuation of International Patent Application No. PCT/US2024/012940, filed Jan. 25, 2024, which claims priority to U.S. Patent Application No. 63/481,535 filed Jan. 25, 2023, which is hereby incorporated by reference in its entirety.

FIELD OF THE INVENTION

The present invention relates to methods of treating Netherton syndrome (e.g., in a patient in need thereof). The methods comprise administering to the patient a serine protease inhibitor and an anti-inflammatory agent. The present invention also relates to pharmaceutical compositions (e.g., topical pharmaceutical compositions) comprising a serine protease inhibitor and an anti-inflammatory agent.

BACKGROUND OF THE INVENTION

Netherton syndrome is a disorder that affects the skin, hair, and immune system. Newborns with Netherton syndrome have skin that is red and scaly (ichthyosiform erythroderma), and the skin may leak fluid. Some affected infants are born with a tight, clear sheath covering their skin called a collodion membrane. This membrane is usually shed during the first few weeks of life. Because newborns with this disorder are missing the protection provided by normal skin, they are at risk of becoming dehydrated and developing infections in the skin or throughout the body (sepsis), which can be life-threatening. Affected babies may also fail to grow and gain weight at the expected rate (failure to thrive). The health of older children and adults with Netherton syndrome usually improves, although they often remain underweight and of short stature.

After infancy, the severity of the skin abnormalities varies among people with Netherton syndrome and can fluctuate over time. The skin may continue to be red and scaly, especially during the first few years of life. Some affected individuals have intermittent redness or experience outbreaks of a distinctive skin abnormality called ichthyosis *linearis circumflexa*, involving patches of multiple ring-like lesions. The triggers for the outbreaks are not known, but researchers suggest that stress or infections may be involved.

Itchiness is a common problem for affected individuals, and scratching can lead to frequent infections. Dead skin cells are shed at an abnormal rate and often accumulate in the ear canals, which can affect hearing if not removed regularly. The skin is abnormally absorbent of substances such as lotions and ointments, which can result in excessive blood levels of some topical medications. Because the ability of the skin to protect against heat and cold is impaired, affected individuals may have difficulty regulating their body temperature.

Individuals with Netherton syndrome have hair that is fragile and breaks easily. Some strands of hair vary in diameter, with thicker and thinner spots. This feature is known as bamboo hair, trichorrhexis *nodosa*, or trichorrhexis *invaginata*. In addition to the hair on the scalp, the eyelashes and eyebrows may be affected. The hair abnormality in Netherton syndrome may not be noticed in infancy because babies often have sparse hair.

Most individuals with Netherton syndrome have immune system-related problems such as food allergies, hay fever, asthma, or eczema.

U.S. Publication No. 2013/0338198 discloses a particular skin disorder treatment composition that includes, among other things, a serine protease inhibitor, a hydrophobic polymer/hydrophilic polymer complex comprising a poly (vinylpyrrolidone-alkylene) polymer, a release agent, and water.

There is a need for new methods and compositions for treating Netherton syndrome.

SUMMARY OF THE INVENTION

In one aspect, the present invention relates to a method of treating Netherton syndrome in a patient (e.g., in a patient in need thereof). In one embodiment, the method comprises administering to the patient (e.g., an effective amount of) (i) a serine protease inhibitor and (ii) an anti-inflammatory agent.

In one embodiment, the serine protease inhibitor and anti-inflammatory agent are administered to the patient during an outbreak of Netherton syndrome.

Another aspect is a method of treating Netherton syndrome in a patient (e.g., in need thereof) comprising administering to the patient (e.g., an effective amount thereof)

(a) a serine protease inhibitor and an anti-inflammatory agent, when the patient is having an outbreak of Netherton syndrome; and (b) a serine protease inhibitor when the patient is in remission.

In one embodiment, the outbreak of Netherton syndrome includes ichthyosis *linearis circumflexa.*

In another embodiment, an anti-inflammatory agent is not administered with the serine protease inhibitor when the patient is in remission.

In any of the methods described herein, the serine protease inhibitor alone or in combination with the anti-inflammatory agent are administered in an amount effective to suppress or inhibit the Netherton syndrome or a symptom thereof.

In one embodiment of any of the methods described herein, the serine protease inhibitor and the anti-inflammatory agent are administered topically.

The serine protease inhibitor and anti-inflammatory agent may be administered in a single dosage form (e.g., as a fixed dose combination such as a gel, lotion or cream) or in separate dosage forms, which may be administered concomitantly or sequentially by the same or different routes of administration. The dosage form(s) used can be lotions, creams, gels, or liquids.

Yet another aspect is a pharmaceutical composition (such as a topical pharmaceutical composition, e.g., for use in treating Netherton syndrome) comprising (a) a serine protease inhibitor and (b) an anti-inflammatory agent.

In one embodiment of any of the methods (and compositions for use in treating Netherton syndrome in a patient) described herein, the patient has the SPINK5 mutation.

In a preferred embodiment of any of the methods and compositions described herein, the serine protease inhibitor is dipalmitoyl hydroxyproline or a pharmaceutically acceptable salt thereof.

In one embodiment of any of the methods (and compositions for use in treating Netherton syndrome in a patient) described herein, the serine protease inhibitor and anti-inflammatory agent are topically applied to lesions on the arms and/or lower legs.

In one embodiment of any of the methods and compositions described herein, the anti-inflammatory agent is selected from nonsteroidal anti-inflammatory drugs (such as ibuprofen, meloxicam and diclofenac), corticosteroids (such as prednisolone), TNF antagonists including TNFα and/or β inhibitors (such as adalimumab, infliximab, and etanercept), capsaicin, felbinac, ketoprofen, piroxicam, acetylsalicylic acid, glycyrrhetinic acid, pharmaceutically acceptable salts thereof, and any combination of any of the foregoing. In one embodiment, the anti-inflammatory agent is diclofenac, ketoprofen, pharmaceutically acceptable salts thereof, and any combination of any of the foregoing. In another embodiment, the anti-inflammatory agent is diclofenac or a pharmaceutically acceptable salt thereof (e.g., diclofenac sodium, diclofenac potassium, and diclofenac epolamine). In yet another embodiment, the anti-inflammatory agent is ketoprofen or a pharmaceutically acceptable salt thereof (e.g., ketoprofen).

In one embodiment of any of the compositions described herein, the composition is a topical composition.

DETAILED DESCRIPTION OF THE INVENTION

Disclosed herein are detailed descriptions of specific aspects of the present application. It will be understood that the disclosed embodiments are merely examples of the way in which certain aspects of the application can be implemented and do not represent an exhaustive list of all of the ways the application may be embodied.

Definitions

Throughout this specification it is to be understood that the words "comprise" and "include" and variations such as "comprises," "comprising," "includes," "including" are to be interpreted inclusively, unless the context requires otherwise. The use of these words may imply the inclusion of an element or elements not specifically recited.

As used herein, the terms "treatment" or "treating" relate to curing or substantially curing a condition, as well as ameliorating, delaying, relieving, inhibiting, or reducing at least one symptom of the condition, and are inclusive of prophylactic treatment and therapeutic treatment. As would be recognized by one or ordinary skill in the art, treatment that is administered prior to clinical manifestation of a condition is prophylactic (i.e., it protects the subject against developing the condition). If the treatment is administered after manifestation of the condition, the treatment is therapeutic (i.e., it is intended to diminish, ameliorate, control, or maintain the existing condition and/or side effects associated with the condition).

The term "topical composition" as used herein refers to a composition suitable for application directly to the skin, nail, or mucosal tissue, either by hand or through a suitable applicator. In one embodiment, the term "topical composition" as used herein refers to a composition suitable for application directly to the skin.

The term "patient" or "subject" as used herein refers to, but is not limited to, a human or an animal including mammals (such as monkeys, guinea pig, domestic pets, for instance, cats and dogs).

As used herein, the term "about" when used to refer to weight % in composition or other numeral amounts means plus or minus up to 20% (alternatively, up to 10% or 5%) of the reported value.

The phrases "weight %" "% by weight" and "% w/w" describe the weight percentage(s) of an ingredient based on the total weight of a composition containing the ingredient, unless otherwise indicated.

The term "pharmaceutically acceptable salt(s)" as used herein means salts derived from inorganic bases (such as Li, Na, K, Ca, Mg, Fe, Cu, Zn, and Mn), salts of organic bases (such as N,N'-diacetylethylenediamine, glucamine, triethylamine, choline, hydroxide, dicyclohexylamine, metformin, benzylamine, trialkylamine, thiamine, and the like), salts of chiral bases (such as alkylphenylamine, glycinol, phenyl glycinol and the like), salts of natural amino acids (such as glycine, alanine, valine, leucine, isoleucine, norleucine, tyrosine, cystine, cysteine, methionine, proline, hydroxy proline, histidine, ornithine, lysine, arginine, serine, and the like), salts of non-natural amino acids (such as D-isomers or substituted amino acids), salts of guanidine, salts of substituted guanidine (wherein the substituents are selected from nitro, amino, alkyl, alkenyl, or alkynyl), ammonium salts, substituted ammonium salts, and aluminum salts. Other pharmaceutically acceptable salt(s) include acid addition salts (where appropriate) such as sulphates, nitrates, phosphates, perchlorates, borates, hydrohalides, acetates, tartrates, maleates, citrates, fumarates, succinates, palmoates, methanesulphonates, benzoates, salicylates, benzenesulfonates, ascorbates, glycerophosphates, ketoglutarates and the like. Yet other pharmaceutically acceptable salt(s) include, but are not limited to, quaternary ammonium salts of the compounds of the present invention with alkyl halides or alkyl sulphates (such as MeI and $(Me)_2SO_4$). Pharmaceutically acceptable solvates may be hydrates or comprise other solvents of crystallization such as alcohols.

Serine Protease Inhibitor(s)

A suitable serine protease inhibitor is dipalmitoyl hydroxyproline.

The serine protease inhibitor can also be a LEKTI protein domain as described in U.S. Patent Publication No. 2021/0162029, which is hereby incorporated by reference.

Anti-Inflammatory Agent(s)

Suitable anti-inflammatory agents include nonsteroidal anti-inflammatory drugs (such as ibuprofen, meloxicam and diclofenac), corticosteroids (such as prednisolone), TNF antagonists including TNFα and/or β inhibitors (such as adalimumab, infliximab, and etanercept), capsaicin, felbinac, ketoprofen, piroxicam, acetylsalicylic acid, glycyrrhetinic acid, pharmaceutically acceptable salts thereof, and any combination of any of the foregoing.

In one embodiment, the anti-inflammatory agent is diclofenac, ketoprofen, pharmaceutically acceptable salts thereof, and any combination of any of the foregoing. In another embodiment, the anti-inflammatory agent is diclofenac or a pharmaceutically acceptable salt thereof (e.g., diclofenac sodium, diclofenac potassium, and diclofenac epolamine). In yet another embodiment, the anti-inflammatory agent is ketoprofen or a pharmaceutically acceptable salt thereof (e.g., ketoprofen).

Methods of Treatment

The serine protease inhibitor and anti-inflammatory agent may be administered by any route of administration, such as orally or topically.

In a preferred embodiment, the serine protease inhibitor is administered topically and the anti-inflammatory agent is administered by any route (e.g., orally, parenterally, or topically).

In another preferred embodiment, both the serine protease inhibitor and anti-inflammatory agent are administered topically. For instance, the amount of serine protease inhibitor (such as dipalmitoyl hydroxyproline) provided in a topical composition can be at least 0.0001 wt. %, such as about 0.2 wt. % to about 5 wt. %, about 0.5 wt. % to about 3 wt. %, or about 0.8 wt. % to about 2.5 wt. %, based on the total weight of the topical composition.

In certain embodiments of any of the topical compositions described herein, the topical composition comprises about 0.5 to about 5% w/w of diclofenac or a pharmaceutically acceptable salt thereof (e.g., diclofenac sodium, diclofenac potassium, and diclofenac epolamine), such as about 1%, 1.3%, 1.5%, 2%, or 3% w/w of diclofenac or a pharmaceutically acceptable salt thereof (e.g., diclofenac sodium, diclofenac potassium, and diclofenac epolamine).

In another embodiment, the topical composition includes ketoprofen.

In certain embodiments, any of the topical compositions described herein are topically applied to the area of the subject to be treated at least once a day, such as two, three or four times a day.

In certain embodiments, any of the topical compositions described herein are topically applied to the area of the subject to be treated once a day.

In certain embodiments, any of the compositions described herein are topically applied to the area of the subject to be treated twice a day.

In certain embodiments of any of the topical compositions described herein, the topical composition is an aqueous based composition (i.e., a water-based composition, which is free or substantially free of non-water solvent.) The term "substantially free of non-water solvent" is intended to indicate that the formulation contains less than about 2%, less than about 1%, less than about 0.5% or less than about 0.1% of non-water solvent.

The topical composition can be applied to skin tissue as a result of applying the composition as a cream or lotion to the skin tissue, and rubbing onto the skin tissue. The action of rubbing may include gentle rubbing or vigorous rubbing. In one embodiment, Although the composition is sometimes characterized as having a binding or almost adhesive property with respect to skin tissue, the composition is not the type of composition that one would consider to be an adhesive that holds two substrates together such as, for example, a hot melt adhesive.

In one embodiment, the anti-inflammatory agent is diclofenac or a pharmaceutically acceptable salt thereof (e.g., diclofenac sodium, diclofenac potassium, and diclofenac epolamine), which is orally administered. For instance, about 100 to about 200 mg/day of diclofenac or a pharmaceutically acceptable salt thereof (e.g., diclofenac sodium, diclofenac potassium, and diclofenac epolamine) can be administered in the method described herein.

In another embodiment, the anti-inflammatory agent is ketoprofen or a pharmaceutically acceptable salt thereof (e.g., ketoprofen), which is orally administered. For instance, about 50 to about 300 mg per day (e.g., about 75 to about 300 mg per day) of ketoprofen or a pharmaceutically acceptable salt thereof (e.g., ketoprofen) can be administered in the method described herein.

Pharmaceutical Compositions

The serine protease inhibitor when administered alone may be incorporated in a topical pharmaceutical composition, such as those described in U.S. Pat. No. 2013/0338198.

The topical composition may also include the anti-inflammatory agent.

Any of the pharmaceutical compositions (e.g., topical pharmaceutical compositions) described herein may comprise one or more pharmaceutically acceptable excipients, such as, but not limited to, one or more of a penetration enhancer, a buffering agent, a pH modifier, a surfactant, a thickener, a conditioning agent, a preservative, a chelating agent, a gelling agent, an emulsifier, a foaming agent, a colorant, a solvent, and any combination of any of the foregoing. Suitable excipients that may be used are also described in U.S. Publication No. 2013/0338198, which is hereby incorporated by reference in its entirety.

Suitable penetration enhancers for use in any of the pharmaceutical compositions described herein include, but are not limited to, sulfoxides (e.g. DMSO), azones (e.g. laurocapram), pyrrolidones (e.g., 2-pyrrolidone), alcohols and alkanols (e.g., ethanol, decanol), oleic acid and derivatives thereof, glycols (e.g., propylene glycol), dimethylformamide (DMF), dimethylacetamide (DMAC), fatty alcohols (e.g., lauryl alcohol), fatty acid esters, fatty acids, fatty alcohol ethers (e.g., EO-2-oleyl ether), and terpenes, and any combination of any of the foregoing. In one embodiment, the penetration enhancer may present in a concentration ranging from about 1% to about 20% by weight of the composition.

Suitable buffering agents for use in any of the pharmaceutical compositions described herein include, but are not limited to, phosphates, such as monobasic sodium phosphate, dibasic sodium phosphate, lactates and citrates such as citric acid monohydrate, sodium citrate dihydrate, and any combination of any of the foregoing. The buffering agent may be present in a concentration ranging from about 0.01% to about 5% by weight of the composition.

Suitable pH modifiers for use in any of the pharmaceutical compositions described herein include, but are not limited to, acids such as hydrochloric acid, phosphoric acid, citric acid and lactic acid, and suitable bases such as diethanolamine, triethanolamine and sodium hydroxide, and any combination of any of the foregoing. The pH modifier may be present in a concentration ranging from about 0.01% to about 5% by weight of the composition.

Suitable surfactants include anionic surfactants, non-ionic surfactants, amphoteric surfactants, and any combination of any of the foregoing. Suitable surfactants for use in any of the pharmaceutical compositions described herein include, but are not limited to, sodium laureth sulfate, cocamidopropyl betaine, laureth 2, leuramide mea, tea lauryl sulfate, disodium laureth sulfosuccinate, PEG-120 methyl glucose dioleate, sodium lauryl ether sulfate, lauryl alcohol, polyoxyethylene ether, polyoxyethylene glycerol monostearate, stearic acid ester oxygen polyhydrocarbon, vitamin E succinate polyethylene glycol ester, sorbitan esters, polyoxyethylene castor oil, polyoxyethylene hydrogenated castor oil, poloxamer, organic esters (e.g. ethylene acetate), and polysorbate 80 (i.e., TWEEN® 80), and any combination of any of the foregoing. In one embodiment, the surfactant is present in a concentration ranging from about 1% to about 25% by weight of the composition.

In another embodiment, any of the compositions described herein contain at least 2% w/w of a surfactant, such as at least 5% w/w, at least 7.5% w/w, at least 10% w/w, at least 12.5% w/w, at least 15% w/w, at least 17.5% w/w, at least 20% w/w, at least 22.5% w/w, at least 25% w/w, at least 27.5% w/w, at least 30% w/w, at least 35% w/w or at least 40% w/w of a surfactant. In one embodiment, the surfactant comprises an anionic surfactant, an amphoteric surfactant, or a combination thereof. In another embodiment, the surfactant comprises an anionic surfactant and an amphoteric surfactant. In yet another embodiment, the surfactant comprises an anionic surfactant, an amphoteric surfactant, and a non-ionic surfactant.

Suitable thickeners for use in any of the pharmaceutical compositions described herein include, but are not limited to, polyquaternium-10, sodium chloride, natural plant starch, xanthan gum, arabic gum, guar gum, carrageenin and seaweed gel, and any combination of any of the foregoing. The thickener may be present in a concentration ranging from about 0.1% to about 10.0% by weight of the composition.

Suitable conditioning agents (moisturizers) for use in any of the pharmaceutical compositions described herein include, but are not limited to, citrimonium chloride, laurdimonium hydroxypropyl hydrolyzed collagen and silicone agents, and any combination of any of the foregoing. The conditioning agent may be present in a concentration ranging from about 0.1% to about 10.0% by weight of the composition.

Suitable preservatives for use in any of the pharmaceutical compositions described herein include, but are not limited to, chloro-m-cresol, citric acid, disodium edetate, ethoxylated alcohol, glycerin, 1,2,6-hexanetriol, methylparaben, parabens, potassium, sorbate, propyl gallate, propylene glycol, propyl paraben, sodium bisulfate, sodium citrate, butyl paraben, sodium metabisulfite, chlorocresol, sorbic acid, tannic acid, zinc stearate, butylated hydroxytoluene, butylated hydroxyanisole, benzoic acid, salicylic acid, propyl paraben, dichlorobenzyl alcohol, formaldehyde, alphatocopherol, sodium ascorbate, ascorbic acid, ascorbyl palmitate phenol, m-cresol, bisphenol, cetrimide, benzalkonium chloride, sorbic acid, phenoxyethanol, imidurea, benzyl alcohol and benzoyl peroxide, and any combination of any of the foregoing. The preservative may be present in a concentration ranging from about 0.1% to about 10.0% by weight of the composition.

Suitable chelating agents for use in any of the pharmaceutical compositions described herein include, but are not limited to, ethylenediaminetetraacetic acid (EDTA), citric acid, diethylenetriaminepentaacetic acid (DTPA), deferoxamine, deferasirox, deferiprone, pyridoxal isonicotinoyl hydrazone, rhodotorulic acid, picolinic acid, nicotinic acid, neoaspergillic acid, methionine, lactic acid, N,N-ethylene bis[N-phopsphonomethyl]glycine, tetraethylenepentaamine heptaacetic acid (TPHA), tri(2-aminoethyl)aminehexaacetic acid (TAAHA), triethylenetetraaminehexaacetic acid (TTHA), oxybis(ethylenenitrilo)tetraacetic acid (BAETA), trans-1,2-cyclohexaneediaminetetraacetic acid, salicyclic acid, tartaric acid, 2,3-dihydroxybenzoic acid, penicillamine, etidronic acid (1-hydroxyethan-1,1-diyl)bis(phosphonic acid), dimercaptosuccinic acid, dimercapto-propane sulfonate, dimercaprol, desferrithiocin (DFT), polycarboxylates, hydroxamates, catecholates, hydroxypyridonates, and teraphthalamides, and any combination of any of the foregoing. The chelating agent may be present in a concentration ranging from about 0.01% to about 5% by weight of the composition.

Suitable gelling agents for use in any of the pharmaceutical compositions described herein include, but are not limited to, carboxypolymethylene (Carbopol), carboxycelluloses (such as sodium carboxymethylcellulose), hydroxycelluloses (such as hydroxypropylcellulose and hydroxymethylcellulose), acrylates and alkyl acrylates (such as mixtures of cross~linked crylate and C10~30 alkyl acrylate copolymers), carrageenin, alginates, dextrins, dextrans, gelatins and xanthan gum, and any combination of any of the foregoing. The gelling agent may be present in a concentration ranging from about 0.1% to about 5% by weight of the composition.

Suitable emulsifiers for use in any of the pharmaceutical compositions described herein include, but are not limited to, oleyl alcohol, polyoxyethylene oleyl ether, PEG-40 stearate, ceteareth-12, ceteareth-20, ceteareth-30, glyceryl stearate, PEG-100 stearate, PEG 75 Lanolin, methyl myristate, isopropyl myristate, Arlacel 165, glyceryl stearate, PEG-100 stearate, steareth-2 and steareth-20, dimethicone copolyol, Polysorbate 20 (Tween 20), cetyl esters wax, Polysorbate 40 (Tween 40), Polysorbate 60 (Tween 60), Polysorbate 80 (Tween 80), lauramide DEA, cocamide DEA, and cocamide MEA, Phospholipid PTC, alginate, carrageenan, Glucate DO, methylcellulose, polyvinyl alcohol, Carbopol and Carbomer, and any combination of any of the foregoing. The emulsifier may be present in a concentration ranging from about 0.1% to about 5% by weight of the composition.

Suitable foaming agents for use in any of the pharmaceutical compositions described herein include, but are not limited to, coconut fatty acid diethanolamide, ethoxylated sorbitan stearate, palmitate, oleate, nonyl phenol ethoxylates and fatty alcohol ethoxylates, and any combination of any of the foregoing. The foaming agent may be present in a concentration ranging from about 0.5% to about 10% by weight of the composition.

Suitable solvents for use in any of the pharmaceutical compositions described herein include, but are not limited to, water, butylene glycol, propylene glycol, propylene carbonate, caproyl 90, DMSO, ethyl acetate and diethylene glycol monoethyl ether, and any combination of any of the foregoing.

Any of the pharmaceutical composition described herein may further comprise a solubilizing agent. Suitable solubilizing agents for use in any of the pharmaceutical compositions described herein include, but are not limited to, butylene glycol, propylene glycol, propylene carbonate, propylene glycol caprylate (such as propylene glycol monocaprylate (type II) (Caproyl 90 available from Gattefossé of Saint-Priest, France)), DMSO, ethyl acetate and diethylene glycol monoethyl ether, and any combination of any of the foregoing. The solubilizing agent may be present in a concentration ranging from about 0.1% to about 30% by weight of composition.

In one embodiment, any of the topical compositions described herein further comprises a skin bonding polymer component, and a barrier component. The skin bonding polymer component holds the active agents together with the barrier component, and the barrier component is at least in part responsible for providing barrier properties when the composition is applied to skin.

One Topical Serine Protease Inhibitor—Anti-Inflammatory Agent Composition

In one embodiment, the topical composition comprises (a) about 0.0001 wt. % to about 5 wt. % of a serine protease inhibitor, (b) an anti-inflammatory agent (e.g., about 0.0001 wt % to about 25 wt. %), (c) about 2 wt. % to about 10 wt. % of a hydrophobic polymer/hydrophilic polymer complex comprising a poly(vinylpyrrolidone-alkylene) polymer wherein the alkylene group contains at least 10 carbon atoms (e.g., a poly(vinylpyrrolidone-alkylene) polymer wherein the alkylene group contains at least 10 carbon atoms and a poly(maleic acid/methylvinylether) copolymer) and optionally a cellulose containing polymer, (d) about 0.5 wt. % to about 20 wt. % of a barrier component or about 0.5 wt. % to about 5 wt. % of a release agent, and (e) at least about 50 wt. % water.

The hydrophobic polymer/hydrophilic polymer complex (polymer component) of the topical composition can be provided as a component that exhibits a tendency to bond to skin tissue, and hold the serine protease inhibitor in place and allow the serine inhibitor to be released at a desired rate. When the polymer component is provided as a polymer that has a tendency to bond to skin tissues, the polymer component can be characterized as a skin bonding polymer component.

The polymer component can be prepared from a topical composition precursor. The topical composition precursor can be prepared by melt processing a hydrophobic polymer composition and a hydrophilic polymer composition to provide an interaction between the hydrophobic polymer composition and the hydrophilic polymer composition. It should be understood that the phrase "melt processing" refers to mixing the hydrophobic polymer composition and the hydrophilic polymer composition under conditions that provide that the hydrophobic polymer component of the hydrophobic polymer composition and the hydrophilic polymer component of the hydrophilic polymer composition are in a fluid (i.e., liquid) state so that they sufficiently mix. When the polymers are sufficiently mixed, it is believed that an interaction forms between the hydrophobic polymer component and the hydrophilic polymer component. The melt processing temperature can be at least about 50° C. and can be at least about 70° C. to generate this interaction. In addition, the melt processing temperature can be at least about 80° C. or at least above 90° C., but should not be so high that it causes degradation of the polymers.

The result of the interaction between the hydrophobic polymer component and the hydrophilic polymer component can be referred to as a hydrophobic polymer/hydrophilic polymer adduct. The term "adduct" is used to refer to the interaction between the hydrophobic polymer component and the hydrophilic polymer component. The interaction may be a form of complexing, but that is only theory. Accordingly, the term "adduct" is not meant to limit the polymer component to a particular theory of interaction. The interaction, however, provides an emulsion containing the adduct with an enhanced shelf life compared with an emulsion where an adduct has not been formed. An emulsion containing the adduct can exhibit enhanced resistance to splitting into separate phases. It has been found that an emulsion formed by simply mixing the hydrophobic polymer composition and the hydrophilic polymer composition under conditions so that the adduct is not formed results in a composition that has a greater tendency to split into separate phases.

In one embodiment, the interaction between the hydrophobic polymer component and the hydrophilic polymer component is achieved in the absence of water.

The polymer component can include a hydrophobic polymer/hydrophilic polymer adduct and can include other components. Polymer components that can be used according to the invention can include the polymer components disclosed in U.S. Pat. No. 6,756,059. The entire disclosure of U.S. Pat. No. 6,756,059 is incorporated herein by reference.

The polymer component of the composition can be, at least in part, responsible for holding or isolating the serine protease inhibitor. By binding to skin tissue and holding on to the serine protease inhibitor, the polymer component can help deliver the serine protease inhibitor to the skin tissue to provide a desired level of activity for a desired length of time. For example, the composition can be provided so that it adheres or binds to skin tissue for at least about one hour, and preferably at least about two hours, and holds the serine protease inhibitor for that length of time so that the serine protease inhibitor remains active for that length of time.

The hydrophobic polymer composition includes at least one hydrophobic polymer and can include a mixture of hydrophobic polymers. The hydrophobic polymer composition can include components having repeating pyrrolidone/alkylene groups. Exemplary polymers having repeating pyrrolidone/alkylene groups include poly(vinylpyrrolidone/alkylene) polymers. Poly(vinylpyrrolidone/alkylene) polymers include those polymers obtained by polymerizing alkylene substituted vinylpyrrolidone. Poly(vinylpyrrolidone/alkylene) polymers can be represented by the following general formula:

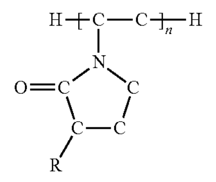

wherein R represents a carbon chain such as an alkylene group and n represents the number of repeating units. The R group is preferably sufficiently long so that the polymer remains relatively water insoluble and should not be too long so that the polymer is difficult to melt process. The alkylene group can contain at least about 10 carbon atoms and can contain less than about 30 carbon atoms. The alkylene group can contain about 14 carbon atoms to about 22 carbon atoms, and can contain about 15 carbon atoms to about 19 carbon atoms.

The poly(vinylpyrrolidone/alkylene) polymers can have a molecular weight that is sufficiently high so that the polymer maintains its water insolubility but the molecular weight should not be so high that it becomes difficult to melt process the polymer. The weight average molecular weight of the poly(vinylpyrrolidone/alkylene) polymer can be between about 3,000 and about 400,000. Another way to characterize the size of the poly(vinylpyrrolidone/alkylene) polymer is by the number of repeating units (n). In the case of a poly(vinylpyrrolidone/alkylene) polymer having a weight average molecular weight of about 6,000 to about 30,000, the poly(vinylpyrrolidone/alkylene) polymer can have about 20 to about 80 repeating units, and can have about 30 to about 50 repeating units. It should be understood that repeating units refer to the residues of vinylpyrrolidone/alkylene groups.

Exemplary poly(vinylpyrrolidone/alkylene) polymers include poly(vinylpyrrolidone/1-eicosene) and poly(vinylpyrrolidone/hexadecene).

Poly(vinylpyrrolidone/1-eicosene) can be referred to as PVPE and is commonly used in pharmaceutical and cosmetic preparations. An exemplary form of PVPE for use according to the invention includes about 43 to 44 repeating units in length and has a weight average molecular weight of about 17,000 and can be characterized as a paraffin-like solid. This particular PVPE is highly insoluble in water, and has an extremely low oral toxicity ($LD_{50}$>17000 mg/kg) and exhibits no demonstrable dermal toxicity. Poly(vinylpyrrolidone/1-hexadecene) can be referred to as PVPH. An exemplary form of PVPH is available as a viscous yellow liquid that is insoluble in water and has a low oral toxicity ($LD_{50}$>64000 mg/kg), has about 39 to 40 repeating units, a molecular weight of about 14,000, and exhibits no demonstrable dermal toxicity.

PVPE and PVPH differ in the length of the hydrocarbon side chain, and are used extensively in the skin care industry, usually at concentrations of less than 1% by weight, because of their ability to bind to skin. Because the skin care industry generally prefers to apply actives to skin using a water-based composition, the use of PVPE and PVPH often requires solvents, surfactants, and emulsifiers to stabilize these polymers in a water emulsion. However, many of the solvents, surfactants and emulsifiers used to stabilize PVPE and PVPH in a water emulsion lack the low dermal toxicities of PVPE and PVPH. PVPE and PVPH by themselves lack a cosmetically elegant appeal when applied directly to the skin. They tend to be sticky and greasy.

The hydrophobic polymer composition can be provided as a single poly(vinylpyrrolidone/alkylene) polymer or as a mixture of different poly(vinylpyrrolidone/alkylene) polymers. The mixture of different poly(vinylpyrrolidone/alkylene) polymers can include at least 5 wt. % of a first poly(vinylpyrrolidone/alkylene) polymer based on the weight of the hydrophobic polymer composition. The hydrophobic polymer composition can include about 5 wt. % to about 54 wt. % of the first poly(vinylpyrrolidone/alkylene) polymer. The second poly(vinylpyrrolidone/alkylene) polymer can be provided in an amount of at least about 46 wt. % and can be in a range of about 46 wt. % to 95 wt. % based on the weight of the hydrophobic polymer composition. For a hydrophobic polymer composition containing a first poly (vinylpyrrolidone/alkylene) polymer and a second poly(vinylpyrrolidone/alkylene) polymer, the mole ratio of the first polymer to the second polymer can be about 1:22 to about 1:1. When the hydrophobic polymer composition contains a mixture of different poly(vinylpyrrolidone/alkylene) polymers, the poly(vinylpyrrolidone/alkylene) polymers can be selected to provide improved properties compared to a composition having a hydrophobic polymer composition containing a single poly(vinylpyrrolidone/alkylene) polymer.

When the hydrophobic polymer composition is provided as a mixture of PVPH and PVPE, the PVPH can be provided in a range of about 46 wt. % to about 95 wt. % and the PVPE can be provided in a range of about 5 wt. % to about 65 wt. %, based upon the weight of the hydrophobic polymer composition.

The hydrophilic polymer composition can include a poly (maleic acid/methylvinylether) copolymer or a mixture of poly(maleic acid/methylvinylether) copolymers. Poly(maleic acid/methylvinylether) copolymers that can be used can have a weight average molecular weight of at least about 50,000, and can have a weight average molecular weight of about 50,000 to about 4,000,000. The weight average molecular weight can be about 70,000 to 2,500,000. A general structural representation of a poly(maleic acid/methylvinylether) copolymer is shown below:

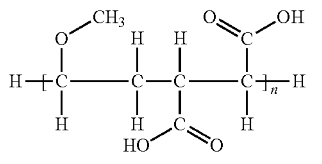

wherein n is the number of repeating units. The number n can be about 200 to about 20,000.

The hydrophilic polymer composition can include a cellulose containing polymer, and can include a mixture of cellulose containing polymers. Cellulose containing polymers that can be used include cellulose, carboxymethyl cellulose, or mixtures thereof. The hydrophilic polymer should have a molecular weight that is not too high so that the hydrophilic polymer becomes difficult to process. The weight average molecular weight of the hydrophilic polymers is preferably sufficient to provide solubility in water but not too high to become difficult to process. Cellulose that can be used can have a weight average molecular weight of about 50,000 to about 15,000,000. An exemplary cellulose component that can be used includes cellulose gum.

The melting temperature refers to the temperature at which the polymer melts, and the maximum temperature refers to the temperature at which the polymer begins to decompose. Exemplary carboxymethyl cellulose polymers that can be used include those having a melting temperature range of about 55° C. to about 60° C. and a maximum temperature range of about 75° C. to about 80° C.

The hydrophobic polymer composition and the hydrophilic polymer composition can be combined and heated to provide a melt and mixed. They can be heated to at least about 50° C. under mixing to form a complex between the hydrophobic and hydrophilic polymers. Preferably, the composition can be heated to at least about 70° C. under mixing to form a complex between the hydrophobic and hydrophilic polymers. It should be understood that a polymer melt refers to a polymer that flows or becomes fluid or liquid when heated and is not meant to refer to a polymer that forms a liquid as a result of being dissolved in a solvent.

The complex formation step can be carried out in a relatively anhydrous environment. Once the desired level of complex formation has occurred, the composition can be hydrated with water. It has been found that the presence of water during the complex formation step can have a deleterious effect on the complex formation process. The reason for this may be that water is ionic and, as a result, can have a tendency to reduce the interaction between the hydrophobic polymer component and the hydrophilic polymer component when they are melt mixed. Accordingly, it is desirable to limit the amount of water present during the complex formation step to a level that does not significantly interfere with the complex formation step or prevent the formation of a complex. In general, this level is typically less that about 1 wt. % water. Preferably, the amount of water is limited to less that about 0.5 wt. %. It should be understood that the reference to the amount of water refers to free water.

The hydrophobic polymer composition and the hydrophilic polymer composition can be mixed together in amounts sufficient to provide a ratio of pyrrolidone groups to hydrophilic groups of about 1:1 to about 5:1. The ratio of the structures causing the observed interaction between the hydrophobic polymer composition and the hydrophilic polymer composition can be referred to as "functional group parity." The ratio of pyrrolidone groups to the combination of carboxylic acid groups and hydroxyl groups can be about 1.5:1 to about 3:1. In order to drive the complex formation reaction, it is desirable to provide an imbalance between the two types of groups. Accordingly, it is generally desirable to provide more of the pyrrolidone groups than the hydrophilic groups.

During the complex formation step, the amounts of hydrophobic polymer composition and hydrophilic polymer composition can be characterized on a weight percent basis. For example, about 2 wt. % to about 28 wt. % hydrophilic polymer composition and about 72 wt. % to about 98 wt. % hydrophobic polymer composition can be combined to provide for complex formation. About 8 wt. % to about 25 wt. % hydrophilic polymer composition and about 72 wt. % to about 95 wt. % hydrophobic polymer composition can be combined to form the complex. During the complex formation step, the amount of water available in the composition can be less than about 1 wt. %. Although the complex forming composition can be relatively anhydrous, it is expected that the amount of water can be between about 0.3 wt. % and about 1.0 wt. %. It should be understood that the amount of water refers to free water.

Once the hydrophobic polymers and the hydrophilic polymers have sufficiently reacted or interacted to form a complex, water can be added to the composition to provide a stable aqueous composition that can be relatively easily further hydrated. It has been found that the first hydration of the topical composition precursor is the most difficult hydration step because of the need to control the conditions of hydration. After the first hydration to a water content of at least about 30 wt. %, it is expected that further hydrations to higher water contents are relatively easy and can be accomplished by simply mixing the composition with water. Accordingly, the amount of water provided in the composition when made available as a concentrate for shipment is preferably between about 30 wt. % and about 45 wt. %. When the composition includes about 30 wt. % to about 45 wt. % water, it is expected that the composition can include about 3 wt. % to about 10 wt. % hydrophilic polymer composition and about 30 wt. % to about 50 wt. % hydrophobic polymer composition.

Water can be added to the relatively anhydrous composition by mixing water and the relatively anhydrous composition at a temperature and for a time sufficient to allow the composition to become hydrated without losing significant amounts of interaction between the hydrophobic polymer composition and the hydrophilic polymer composition. The relatively anhydrous composition can be hydrated by heating to at least 60° C. and adding water while mixing. The composition can be heated to at least about 65° C. and to at least about 70° C. An exemplary temperature range is about 65° C. to about 80° C.

The relatively anhydrous composition can be referred to as the topical composition precursor and generally refers to the hydrophobic polymer/hydrophilic polymer adduct containing less than about 1.0 wt. % water if any water is present. The polymer component for the composition can refer to a composition that contains only the hydrophobic polymer/hydrophilic polymer adduct, and it can refer to a composition wherein the hydrophobic polymer/hydrophilic polymer adduct is diluted with water. In general, it is desirable to have a sufficient amount of water in the polymer component that allows one to formulate the polymer component into the cationic pharmaceutically active ingredient containing composition according to the invention. If there is too little water in the polymer component, it may become difficult to formulate the composition. For example, the polymer component can contain water in an amount of up to about 95 wt. % and may contain water in an amount up to about 97 wt. %. The polymer component can have a water concentration of about 30 wt. % to about 45 wt. %.

Additional components can be added to the hydrophobic polymer/hydrophilic polymer adduct. For example, it may be desirable to add a component that helps stabilize the hydrophobic polymer/hydrophilic polymer adduct, and to help preserve and/or maintain the composition.

An exemplary polymer component that can be used is available under the name Invisicare™ C-5 composition from Skinvisible Pharmaceuticals, Inc. Invisicare™ C-5 composition contains a mixture of poly(vinylpyrrolidone/eicosene) and poly(vinylpyrrolidone/hexadecene), and carboxymethyl cellulose. Another exemplary polymer component that can be used is available under the name Invisicare™ M-1 composition from Skinvisible Pharmaceuticals, Inc. Invisicare™ M-1 composition contains a mixture of poly(vinylpyrrolidone/eicosene) and poly(vinylpyrrolidone/hexadecene), and poly(maleic acid/methylvinylether) copolymer. In one embodiment, the polymer component contains poly (maleic acid/methylvinylether) copolymer as it helps assist with the release of the serine protease inhibitor. In another embodiment, when the composition is provided at a neutral pH, the polymer component containing poly(maleic acid/methylvinylether) copolymer tends to exhibit a negative charge. The negative charge on the polymer component helps facilitate release of a negatively charged active agent.

The polymer component can be provided in the composition in an amount of about 2 wt. % to about 10 wt. % based on the weight of the composition. In addition, the polymer component can be provided in the treatment composition in an amount of about 3 wt. % to about 8 wt. %, 4 wt. % to about 7 wt. %, and about 5 wt. % to about 6 wt. %.

The composition may contain a barrier component to provide the composition with barrier properties. The presence of a barrier component is desirable for treating dermatitis or incontinence. For example, the barrier component can help reduce the passage of body waste such as urine and feces therethrough to help reduce contact of the urine and feces with skin tissue.

An exemplary barrier component is a silicone barrier component such as Dow Corning 9045. When a silicone barrier component is provided in the dermatitis treatment composition, it can be provided in an amount of about 0.5 wt. % to about 20 wt. % based on the weight of the composition. Preferably, the dermatitis treatment composition includes about 0.6 wt. % to about 5 wt. % silicone barrier component based on the weight of the composition. Other exemplary barrier components include allantoin, aluminum hydroxide gel, calamine, cocoa butter, dimethicone, glycerin, kaolin, petrolatum, shark liver oil, white petrolatum, zinc acetate, zinc carbonate, and zinc oxide. When allantoin is used as the barrier component, it can be provided in an amount of about 0.5 wt. % to about 2 wt. % based on the weight of the composition. When aluminum hydroxide gel is provided as the barrier component, it can be provided in an amount of about 0.15 wt. % to about 5 wt. %. When calamine is provided as the barrier component, it can be provided in an amount of about 1 wt. % to about 25 wt. %. When cocoa butter is the barrier component, it can be provided in an amount of 50 wt. % to about 90 wt. %. When dimethicone is provided as a barrier component, it can be provided in an amount of about 1 wt. % to about 30 wt. %. When glycerin is provided as a barrier component, it can be provided in an amount of 20 wt. % to about 45 wt. %. When kaolin is provided as a barrier component, it can be provided in an amount of about 4 wt. % to about 20 wt. %. When petrolatum is provided as a barrier component, it can be provided in amount of about 30 wt. % to about 90 wt. %. When shark liver oil is provided as a barrier component, it can be provided in amount of about 2 wt. % to about 5 wt. %. When white petrolatum is provided as a barrier component, it can be provided in an amount of 30 wt. % to about 90 wt. %. When zinc oxide is provided as a barrier component, it can be provided in amount of about 0.1 wt. % to about 2 wt. %. When zinc carbonate is provided as a barrier component, it can be provided in an amount of about 0.2 wt. % to about 2 wt. %. When zinc oxide is provided as a barrier component it can be provided in an amount of about 1 wt. % to about 25 wt. %. It should be appreciated that mixtures of various barrier components can be provided.

In one embodiment, the topical composition includes a barrier component.

In another embodiment, the topical composition does not include a barrier component.

The composition can include water in an amount sufficient to allow the composition to be applied to skin tissue while providing the desired coverage over the skin tissue. The water component can be provided as deionized water, filtered water, distilled water, reverse osmosis water, or tap water. In the event that the water includes hardness or other components, it may be desirable to include builders, sequestrants, and chelating agents to handle the water hardness. In general, the composition can include at least about 50 wt. % water. In addition, it is expected that if there is too much water, the emulsion might become unstable. In general, the amount of water in the composition can be less than about 95 wt. %. The amount of water in the composition can be about 65 wt. % to about 93 wt. %.

The composition can include pH adjusting agents, buffering agents, or neutralizing agents to provide the composition with a pH that helps stabilize the serine protease inhibitor. Exemplary pH adjusting agents that can be used include sodium hydroxide, potassium hydroxide, triethanolamine, acetic acid, propionic acid, citric acid, succinic acid, and mixtures thereof.

The polymer component of the composition (such as a lotion, cream, gel, or liquid) may be at least in part responsible for reducing the irritability of the composition. For example, it is believed that the polymer component may help reduce irritation of skin tissue. The composition can be provided without any pH modifier, if desired. In general, however, a buffering agent is incorporated into the composition to help control the pH of the composition. Furthermore, the buffering agent is typically selected as a buffering agent that is compatible with skin issue or that does not harm skin tissue.

Thickeners that can be incorporated into the composition include those components that thicken or increase the viscosity of the composition so that the composition can be readily applied to skin. Thickeners that can be used in the composition include those components often referred to as viscosity controlling agents.

Exemplary thickeners or viscosity controlling agents that can be provided in the hand disinfecting composition include cellulose gum, alkane triols; acrylates; substituted celluloses such as hydroxy ethyl cellulose, carboxymethyl cellulose, methylcellulose, and hydroxypropyl cellulose; cetyl alcohol; gums such as natural gums or synthetic gums; long chain alcohols such as those having about 9 to about 24 carbon atoms; polyglycols such as polyethylene glycols, polypropylene glycols, polybutylene glycols, polyethylene propylene glycols, or mixtures thereof; waxes such as natural waxes or synthetic waxes; hydrogenated oils; glycol esters; fatty acid esters; long chain acids; acid amides; silicates; and mixtures thereof. Exemplary thickeners that can be used is hydroxyethyl cellulose. An exemplary thickener that can be used is a polyacrylic acid thickeners available under the name Carbopol, such as, Carbopol Ultrez-10, from Lipscomb.

The composition may or may not include a thickener. When the composition includes a thickener, the thickener can be provided in an amount that provides the desired level of thickening. The composition can include a thickener in an amount of least about 0.1 wt. % and can include a thickener in an amount of at least about 0.4 wt. %. In addition, the thickener can be provided in an amount of less than about 4 wt. %, and can be provided in an amount of less than about 2 wt. %.

The composition can include a release agent to assist with the sustained release of the serine protease inhibitor over a prolonged period of time. The release agent can be provided as a surfactant. A surfactant can additionally be present to help maintain the composition as an emulsion. In general, an emulsion refers to a composition that resists phase separation after sitting at room temperature for a couple of months. In general, it is desirable for the composition to be stored in a warehouse or in a storage closet for at least two months and can remain as an emulsion during that two month period. Preferably, the composition can remain as an emulsion for at least one year or at least two years. The ability of the composition to remain as an emulsion can be tested according to an accelerated stability test where the composition is held at 40° C. for 120 days. It is expected that this accelerated stability test for 120 days roughly corresponds to a period of about two years at room temperature. In general, it is expected that the composition can remain as an emulsion after sitting for two years at room temperature.

Exemplary surfactants that can be used as the surfactant component include nonionic surfactants that help stabilize the emulsion and provide a generally even distribution of the cationic pharmaceutically active ingredient containing component. Exemplary nonionic surfactants that can be used include glycerol stearate such as glycerol monostearate, polysorbate such as that available under the name Tween 80 and Polysorbate 60, polyoxyethylene stearate. In addition, mixtures of nonionic surfactants can be included including mixtures of polysorbate and glycerol stearate. An additional nonionic surfactant that can be used includes an ethoxy surfactant, a propoxy surfactant, or an ethoxy/propoxy surfactant. An exemplary ethoxy/propoxy surfactant includes a 10 carbon chain and 9 PO/EO surfactant available under the name Lutensol XP-90 from BASF. Additional nonionic surfactants include sorbitan monolaurate and sorbitan monostearate. Additional surfactants that can be used include those that are generally characterized as Pluronic surfactants such as poloxamers. Exemplary surfactants that can be used include Pluronic F-87NF and Pluronic L44NF from BASF. In one embodiment, the composition does not include anionic surfactants as they may cause irritation.

The composition can include an amount of surfactant component sufficient to provide the composition with a desired emulsion stability and sufficiently low viscosity without foaming. The amount of the surfactant component in the composition, can be about 0.2 wt. % to about 7 wt. %, about 0.5 wt. % to about 6 wt. %, and about 1 wt. % to about 5 wt. %. It should be understood that the composition can be provided without any surfactant component, if desired.

The composition can contain a release agent to assist with the sustained release of the serine protease inhibitor over a prolonged period of time. A sustained release of the serine protease inhibitor refers to a release, over the time period, wherein the release provides desired properties. In general, it is desirable for the composition to provide a relatively consistent release of the serine protease inhibitor after application of the composition to skin tissue. A relatively consistent release can be characterized as a release rate at one hour that is within about 50% of the release rate at 30 minutes. In addition, a relatively consistent release rate can be characterized as a release rate at two hours that is within about 50% of the release rate at 30 minutes. Preferably, these release rates can be provided within about 25%, and more preferably can be provided within about 15%.

At least two advantages can be obtained by providing a sustained release rate or a relatively constant release rate over a prolonged period of time. For example, by providing a sustained release of the serine protease inhibitor over a prolonged period of time, it is possible to prolong the pharmaceutical efficacy of the composition after application to skin tissue. By prolonging the pharmaceutical efficacy of the composition, it is expected that enhanced performance can be achieved. Furthermore, by controlling the release of the serine protease inhibitor so that it is not released at one instant in time, it is possible to reduce or minimize skin irritation.

The composition can include a non-surfactant release agent in an amount of about 0.2 wt. % to about 7 wt. %.

The composition can include an emollient for improving the texture of the composition. An emollient is an oleaginous or oily substance which helps to smooth and soften the skin, and may also reduce its roughness, cracking or irritation. Exemplary suitable emollients include mineral oil, having a viscosity in the range of 50 to 500 centipoise (cps), lanolin oil, coconut oil, cocoa butter, olive oil, almond oil, macadamia nut oil, synthetic jojoba oils, natural sonora jojoba oils, safflower oil, corn oil, liquid lanolin, aloe vera, cottonseed oil, and peanut oil.

Other suitable emollients include squalane, castor oil, polybutene, odorless mineral spirits, sweet almond oil, avocado oil, clophyllum oil, ricin oil, vitamin E acetate, olive oil, linolenic alcohol, coconut oil, oleyl alcohol, the oil of cereal germs such as the oil of wheat germ, isopropyl palmitate, isopropyl myristate, hexadecyl stearate, butyl stearate, decyl oleate, acetyl glycerides, the octanoates and benzoates of ($C_{12}$-$C_{15}$) alcohols, the octanoates and decanoates of alcohols and polyalcohols such as those of glycol and glycerol, ricin oleates of alcohols and poly alcohols such as those of isopropyl adipate, hexyl laurate and octyl dodecanoate.

Other suitable emollients which are solids or semi-solids at room or ambient temperatures may be used in amounts sufficient to provide liquid topical compositions. Such solid or semi-solid cosmetic emollients include hydrogenated lanolin, hydroxylated lanolin, acetylated lanolin, petrolatum, isopropyl lanolate, butyl myristate, cetyl myristate, myristyl myrislate, myristyl lactate, cetyl alcohol, isostearyl alcohol and isocetyl lanolate. Exemplary emollients include stearic acid, stearyl alcohol, palmitic acid enters natural and synthetic esters such as coconut oil.

The composition can include the emollient in an amount sufficient to provide a silky feel. An exemplary range of the emollient in the composition can be at least about 0.5 wt. %. In addition, the composition can include an emollient in an amount of less than about 3 wt. %. It should be understood that the emollient is an optional component of the composition. The composition can be provided without an emollient, if desired.

The composition can include a moisturizer to provide a desired moisturizing effect to skin tissue. The moisturizer can be provided as a humectant. In general, a humectant is a moistening agent that promotes retention of water due to its hydroscopic properties. Exemplary humectants include glycerine, polymeric glycols such as polyethylene glycol and polypropylene glycol, and sorbitols such as sorbitol solution, pyrrolidone carboxylic acid, urea, or mixtures thereof. The composition can be provided without a moisturizer.

When the composition includes a moisturizer, it can be included in an amount of at least about 0.5 wt. %. In addition, the composition can include a moisturizer in an amount of less than about 5 wt. %.

An additional component that can be provided as part of the composition is a skin soothing agent or component which can also be referred to as a skin protectant. Exemplary skin soothing agents include allantoin, kaolin, cocoa butter, glycerine, shark liver oil, pertolatam, zinc oxide, zinc carbonate, zinc acetate, aluminum hydroxide, calamine, and mixtures thereof.

The skin soothing agent can be provided in the composition in an amount of about 0.2 wt. % to about 2 wt. %, and preferably about 0.5 wt. % to about 1 wt.5.

The composition can include preservatives for prevention of bacterial, fungal, and/or yeast contamination. Exemplary preservatives that can be used in the hand disinfecting composition include phenoxyethanol, benzoic acid, derivatives and salts of benzoic acid, parabens, oxazolidines, chlorinated aromatic compounds and phenols, hydantoins, cresols and derivatives, imiazolindinyl urea, iodopropanol butylcarbamate, sulfites, and bisulfites. The composition can include any of the preservatives commonly used or known to be suitable for topically applied compositions. Exemplary commercially available preservatives include liquid Germal Plus (diazolidinyl urea and iodopropynyl butylcarbamate) and Germaben 11 (diazolidinyl urea and methylparaben and propylparaben).

The composition can be formulated without a preservative. It is expected that the preservative will increase the shelf life of the composition by reducing or preventing the growth of bacteria, fungus, and/or yeast. When the composition includes a preservative, the preservative is preferably provided in an amount sufficient to provide a desired level of protection from growth of bacteria, fungus, and/or yeast.

In general, for most preservatives, it is expected that the amount of preservative can be provided at a level of about 0.1 wt. % to about 1.0 wt. %, and can be provided at a level of about 0.2 wt. % to about 0.5 wt. %, based on the weight of the composition.

The composition can include antioxidants to help increase the shelf life of the composition and to provide desired properties when applied to skin tissue. Exemplary antioxidants that can be used include vitamins such as vitamin E, vitamin E acetate, vitamin C, and vitamin D, and derivatives thereof. Exemplary antioxidants include α-tocopherols which can be characterized as natural or synthetic Vitamin E. Additional exemplary antioxidants include propyl, octyl and dodecyl esters of gallic acid, butylated hydroxyanisole (BHA) (usually as a mixture of ortho and meta isomers), butylated hydroxytoluene (BHT), and nordihydroguaiaretic acid, and alkylated parabens such as methylparaben and propylparaben.

The composition can be formulated without an antioxidant. When the composition includes an antioxidant, the antioxidant can be provided in an amount that provides antioxidant properties in the composition. In general, it is expect that the antioxidant can be provided in an amount of about 0.2 wt. % to about 2 wt. %, and can be provided in an amount of about 0.7 wt. % to about 1.5 wt. %, based on the weight of the composition. In the case of vitamin E, it is expected that the vitamin E can be included in the composition in an amount of about 0.1 wt % to about 1 wt. %, and can be included in an amount of about 0.3 wt. % to about 0.8 wt. %.

Chelating agents are substances used to chelate or bind metallic ions with a certain heterocyclic ring structure so that the ion is held by chemical bonds from each of the participating rings. Suitable chelating agents include ethylene diaminetetraacetic acid (EDTA), EDTA trisodium, EDTA tetrasodium, calcium disodium edetate, EDTA trisodium, EDTA tetrasodium and EDTA dipotassium. One or more chelating agents can optionally be included in the emulsion in amounts ranging from about 0.001 to about 0.1 weight percent. It should be appreciated that the composition can be provided without a chelating agent.

Fragrances are aromatic compounds which can impart an aesthetically pleasing aroma to the composition. Typical fragrances include aromatic materials extracted from botanical sources (i.e. rose petals, *gardenia* blossoms, jasmine flowers, etc.) which can be used alone or in any combination to create essential oils. Alternatively, alcoholic extracts may be prepared for compounding fragrances. One or more fragrances can optionally be included in the composition in an amount ranging from about 0.001 to about 10 weight percent, preferably about 0.05 to about 5 percent. It should be appreciated that the composition can be provided without a fragrance.

The composition may also include non-toxic, pharmaceutically and dermatologically acceptable carriers, diluents and excipients, suitable for topical application, as are well known, see for example Merck Index, Merck & Co., Rahway, N.J., Bioreversible Carriers in Drug Design, Theory and Application, Roche (ed.) Pergamon Press, (1987), Gilman et al., (eds) (1990) Goodman and Gilman's: The Pharmacological Bases of Therapeutics, 8th Ed., Pergamon Press, Novel Drug Delivery Systems, 2nd Ed., Norris (ed.) Marcel Dekker Inc., (1989), and Remington's Pharmaceutical Sciences. For standard dosages of conventional pharmacological agents, see, e.g., Physicians Desk Reference (1997 Edition); and American Medical Association (1997) Drug Evaluations (Subscriptions).

The above specification, examples and data provide a complete description of the manufacture and use of the composition of the invention. Since many embodiments of the invention can be made without departing from the spirit and scope of the invention, the invention resides in the claims hereinafter appended.

EXAMPLES

Topical compositions according to the present invention may include the following components.

Example 1

| Ingredient | Function |
|---|---|
| Serine Protease Inhibitor | Active |
| Anti-Inflammatory Agent | Active |
| Carbopol-Ultrez-10 | Thickener |
| Polysorbate 60 | Release Agent |
| Dow Corning 9045 | Barrier Component |
| Invisicare ™ C-5 Composition | Skin Bonding Polymer |
| Allantoin | Skin Soothing Agent |
| Stearic Acid | Emollient |
| Coconut Oil | Emollient |
| Triethanolamine | pH Adjusting Agent |
| Phenoxyethanol | Preservative |

Example 2

| Ingredient | Function |
|---|---|
| Serine Protease Inhibitor | Active |
| Anti-Inflammatory Agent | Active |
| Carbopol-Ultrez-10 | Thickener |
| Polysorbate 60 | Release Agent |
| EDTA | Chelating Agent |
| Pluronic F-87NF | Release Agent |
| Invisicare ™ C-5 Composition | Skin Bonding Polymer |
| Allantoin | Skin Soothing Agent |
| Stearic Acid | Emollient |
| Coconut Oil | Emollient |
| Triethanolamine | pH Adjusting Agent |
| Phenoxyethanol | Preservative |

Although the invention herein has been described with reference to particular embodiments, it is to be understood that these embodiments are merely illustrative of the principles and applications of the present invention. It is therefore to be understood that numerous modifications may be made to the illustrative embodiments and that other arrangements may be devised without departing from the spirit and scope of the present invention as described above.

All publications and patent applications cited in this application are herein incorporated by reference to the same extent as if each individual publication or patent application was specifically and individually indicated to be incorporated herein by reference.

What is claimed is:

1. A method of treating Netherton syndrome in a patient in need thereof comprising administering to the patient an effective amount of (i) a serine protease inhibitor and (ii) an anti-inflammatory agent, wherein the serine protease inhibitor is dipalmitoyl hydroxyproline or a pharmaceutically acceptable salt thereof.

2. The method of claim 1, wherein the serine protease inhibitor and the anti-inflammatory agent are administered to the patient during an outbreak of Netherton syndrome.

3. The method of claim 1, wherein the method comprises administering an effective amount of a serine protease inhibitor and an anti-inflammatory agent to suppress the Netherton syndrome.

4. The method of claim 1, wherein the patient has the SPINK5 mutation.

5. The method of claim 1, wherein the serine protease inhibitor is dipalmitoyl hydroxyproline.

6. The method of claim 1, wherein the serine protease inhibitor and anti-inflammatory agent are topically applied to lesions on the arms and/or lower legs.

7. The method of claim 1, wherein the anti-inflammatory agent is selected from nonsteroidal anti-inflammatory drugs, corticosteroids, TNF antagonists, capsaicin, felbinac, ketoprofen, piroxicam, acetylsalicylic acid, glycyrrhetinic acid, or a pharmaceutically acceptable salt thereof, or any combination of any of the foregoing.

8. The method of claim 1, wherein the anti-inflammatory agent is selected from diclofenac, ketoprofen, pharmaceutically acceptable salts thereof, or any combination of any of the foregoing.

9. The method of claim 8, wherein the anti-inflammatory agent is diclofenac or a pharmaceutically acceptable salt thereof.

10. The method of claim 8, wherein the anti-inflammatory agent is ketoprofen or a pharmaceutically acceptable salt thereof.

* * * * *